US009945813B2

(12) United States Patent
McIntyre et al.

(10) Patent No.: US 9,945,813 B2
(45) Date of Patent: Apr. 17, 2018

(54) CHEMICAL CALIBRATION PROCESS, SYSTEM AND DEVICE

(71) Applicant: Smiths Detection-Watford Limited, Watford Hertfordshire (GB)

(72) Inventors: Henry McIntyre, Watford Hertfordshire (GB); Neal Thathapudi, Watford Hertfordshire (GB); Paul Arnold, Watford Hertfordshire (GB)

(73) Assignee: Smiths Detection-Watford Limited (GB)

( * ) Notice: Subject to any disclaimer, the term of this patent is extended or adjusted under 35 U.S.C. 154(b) by 0 days.

(21) Appl. No.: 15/310,028

(22) PCT Filed: May 14, 2015

(86) PCT No.: PCT/GB2015/051431
§ 371 (c)(1),
(2) Date: Nov. 9, 2016

(87) PCT Pub. No.: WO2015/173579
PCT Pub. Date: Nov. 19, 2015

(65) Prior Publication Data
US 2017/0241950 A1 Aug. 24, 2017

(30) Foreign Application Priority Data
May 14, 2014 (GB) .................................. 1408593.0

(51) Int. Cl.
*G01N 27/62* (2006.01)
*H01J 49/06* (2006.01)
(Continued)

(52) U.S. Cl.
CPC ........ *G01N 27/622* (2013.01); *H01J 49/0009* (2013.01); *H01J 49/0036* (2013.01); *H01J 49/062* (2013.01); *G01N 2001/2893* (2013.01)

(58) Field of Classification Search
CPC .......... G01N 27/622; G01N 2001/2893; H01J 49/0009; H01J 49/0036; H01J 49/062
(Continued)

(56) References Cited

U.S. PATENT DOCUMENTS 5,450,193 A * 9/1995 Carlsen .................. A61B 5/083
356/246
5,455,417 A 10/1995 Sacristan
(Continued)

FOREIGN PATENT DOCUMENTS

WO 2014045067 A1 3/2014

OTHER PUBLICATIONS

International Search Report dated Sep. 8, 2015 for PCT/GB2015/051431.
(Continued)

*Primary Examiner* — Nicole Ippolito
(74) *Attorney, Agent, or Firm* — Advent, LLP

(57) ABSTRACT

The present application is directed to a process for calibrating a detection apparatus, especially an ion mobility spectrometer, using isoflurane (CAS Reg. No. 26675-46-7) as a chemical standard whereby calibrating the detection apparatus for a known target chemical is based on an evaluation of the experimental data collected for the negative isoflurane monomer ion against the experimental data collected for the negative isoflurane dimer ion.

20 Claims, 7 Drawing Sheets

(51) Int. Cl.
*H01J 49/00* (2006.01)
*G01N 1/28* (2006.01)

(58) Field of Classification Search
USPC ............... 250/423 R, 424, 281, 282, 288
See application file for complete search history.

(56) References Cited

U.S. PATENT DOCUMENTS

| | | | |
|---|---|---|---|
| 6,291,821 B1 | 9/2001 | Danylewych-May et al. | |
| 2006/0078502 A1* | 4/2006 | Dewanjee ............ | A61K 49/101 424/9.361 |
| 2012/0288537 A1* | 11/2012 | Schwendeman . | A61K 47/48015 424/400 |
| 2016/0272940 A1* | 9/2016 | Chung ................... | A61K 35/30 |

OTHER PUBLICATIONS

Search Report dated Nov. 6, 2014 for Application No. GB1408593.0.

Donovan, A. et al., "Oxford miniature vaporiser output with reversed gas flows", Anaesthesia, vol. 62, No. 6, Jun. 2007, pp. 609-614.

Eiceman, G. A. et al., "Ion mobility spectrometry of halothane, enflurane, and isoflurane anesthetics in air and respired gases", Analytical Chemistry, vol. 61, No. 10, May 15, 1989, pp. 1093-1099.

Fernandez-Maestre et al., "Chemical standards in ion mobility spectrometry", The Analyst [on line] vol. 135, 2010, pp. 1433-1442.

Fernandez-Maestre, R. et al., "Chemical standards in ion mobility spectrometry", Analyst, vol. 135, No. 6, Jan. 2010, p. 1433.

Rosenblatt et al., "Application of ion mobility analysis method to surgical anesthesia gas monitoring", Proceedings of the IEEE 22nd Annual Northeast Bioengineering Conference [on line], Mar. 1996, pp. 48-49.

Severinghaus, J. W. et al., "A gas mixer for computer calibration of an anesthetic mass spectrometer", Journal of Clinical Monitoring, vol. 2, No. 4, Oct. 1986, pp. 223-229.

Yang et al., "Simultaneous determination of fluorinated inhalation anesthetics in blood by gas chromatography mass spectrometry combined with a headspace autosampler", Journal of Chromatography B [on line], vol. 759, 201, pp. 307-318.

* cited by examiner

FIG. 1        Calibration flow chart
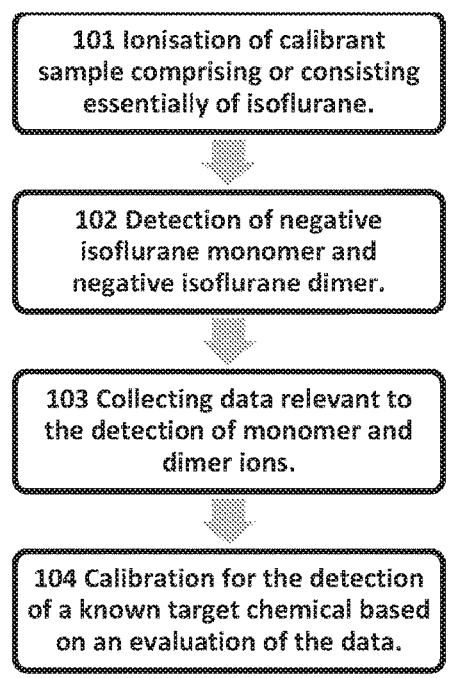
FIG. 2
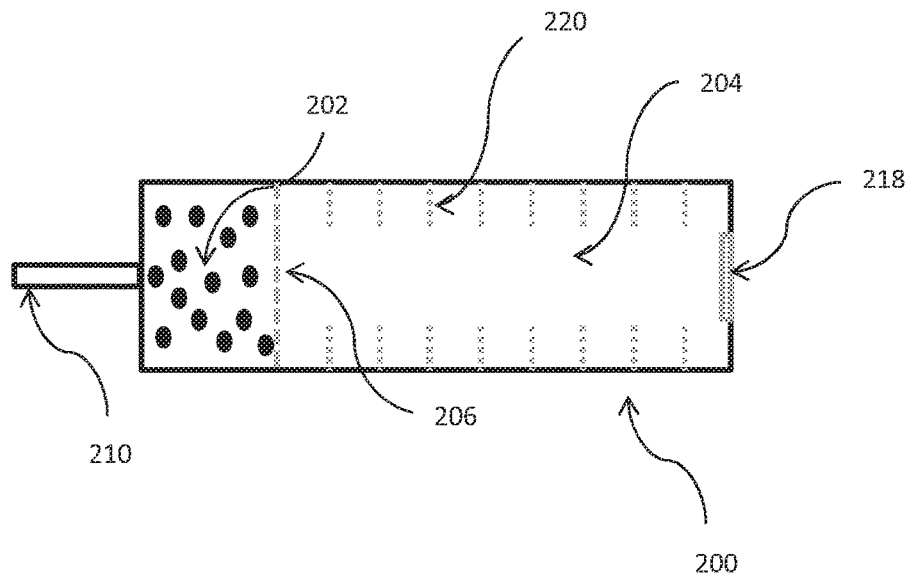

CHEMICAL CALIBRATION PROCESS, SYSTEM AND DEVICE

The present disclosure relates to a process for calibrating a detection apparatus for the detection of target chemicals. More particularly, the disclosure relates to a process comprising use of isoflurane as a chemical standard for calibrating a detection apparatus comprising an ioniser and detector for detecting ions formed as a result of ionisation.

Chemical standards are utilised in a wide range of applications, commonly as a tool for calibrating a device or system. "Calibration" according to the International Bureau of Weights and Measures is defined as an: "operation that, under specified conditions, in a first step, establishes a relation between the quantity values with measurement uncertainties provided by measurement standards and corresponding indications with associated measurement uncertainties (of the calibrated instrument or secondary standard) and, in a second step, uses this information to establish a relation for obtaining a measurement result from an indication". Calibration is thus commonly relied upon as a means for mitigating the effects of variation in experimental conditions, such as pressure and temperature, on the measurement of parameters in a device or system, thereby improving confidence in experimentally obtained data.

In a detection apparatus, confidence in experimentally obtained data is a fundamental requirement and can be of critical importance depending on its application. For instance, detection apparatuses may be employed by military, police and security personnel as a means for detecting chemical warfare agents or alternatively by medical professionals for detecting certain biological materials. Despite their potential for improving the operation and application of a detection apparatus, examples of useful chemical standards which can be relied upon as a means for ensuring that experimental data obtained in relation to a particular analyte sample are relevant and reliable, remain few and far between.

This disclosure relates to the application of 1-chloro-2,2, 2-trifluoroethyl difluoromethyl ether, also known as isoflurane (CAS number: 26675-46-7), as a chemical standard for calibrating a detection apparatus.

In an aspect of the disclosure, there is provided a process for calibrating a detection apparatus comprising: an ioniser for ionising a sample; a detector for detecting ions formed as a result of ionisation; and said process comprising:
i) introducing a calibrant sample comprising isoflurane into the detection apparatus;
ii) collecting experimental data relevant to the detection of negative isoflurane monomer and dimer ions formed as a result of ionisation of the calibrant sample; and
iii) calibrating the detection apparatus for the detection of a known target chemical based on an evaluation of the experimental data collected for the negative isoflurane monomer ion against the experimental data collected for the negative isoflurane dimer ion.

In another aspect of the disclosure, there is provided a system for calibrating a detection apparatus, wherein the detection apparatus comprises: an ioniser for ionising a sample and a detector for detecting ions formed as a result of ionisation; a calibrant sample comprising isoflurane; and an analysis unit configured to:
i) collect experimental data relevant to the detection of isoflurane monomer and dimer ions formed as a result of ionisation of the calibrant sample; and
ii) calibrate the detection apparatus for the detection of a known target chemical based on an evaluation of the experimental data collected for the isoflurane monomer ion against the experimental data collected for the isoflurane dimer ion.

In a further aspect of the disclosure, there is provided a device comprising: a detection apparatus, wherein the detection apparatus comprises: an ioniser for ionising a sample and a detector for detecting ions formed as a result of ionisation; a calibrant sample comprising or consisting essentially of isoflurane; and a means configured for introducing the calibrant sample into the detection apparatus in response to a change in temperature, pressure and/or electric field of the detection apparatus.

In yet a further aspect of the disclosure, there is provided a use of a calibrant sample comprising or consisting essentially of isoflurane for calibrating a detection apparatus for the detection of a target chemical, wherein the detection apparatus comprises: an ioniser for ionising a sample and a detector for detecting ions formed as a result of ionisation.

Embodiments of the disclosure will now be described, by way of example only, with reference to the accompanying Figures, in which:

FIG. 1 corresponds to a flow chart illustrative of the process of the present disclosure.

FIG. 2 shows a detection apparatus in the form of an ion mobility spectrometer in accordance with an embodiment of the present disclosure.

FIG. 3 corresponds to a series of spectra showing drift times of the isoflurane monomer and dimer ion peaks, as well as a reactant ion peak (RIP) resulting from ionisation of air, obtained in the undoped negative mode of an ion mobility spectrometer, whilst internal levels of humidity in the IMS cell are increased.

Figure 3:
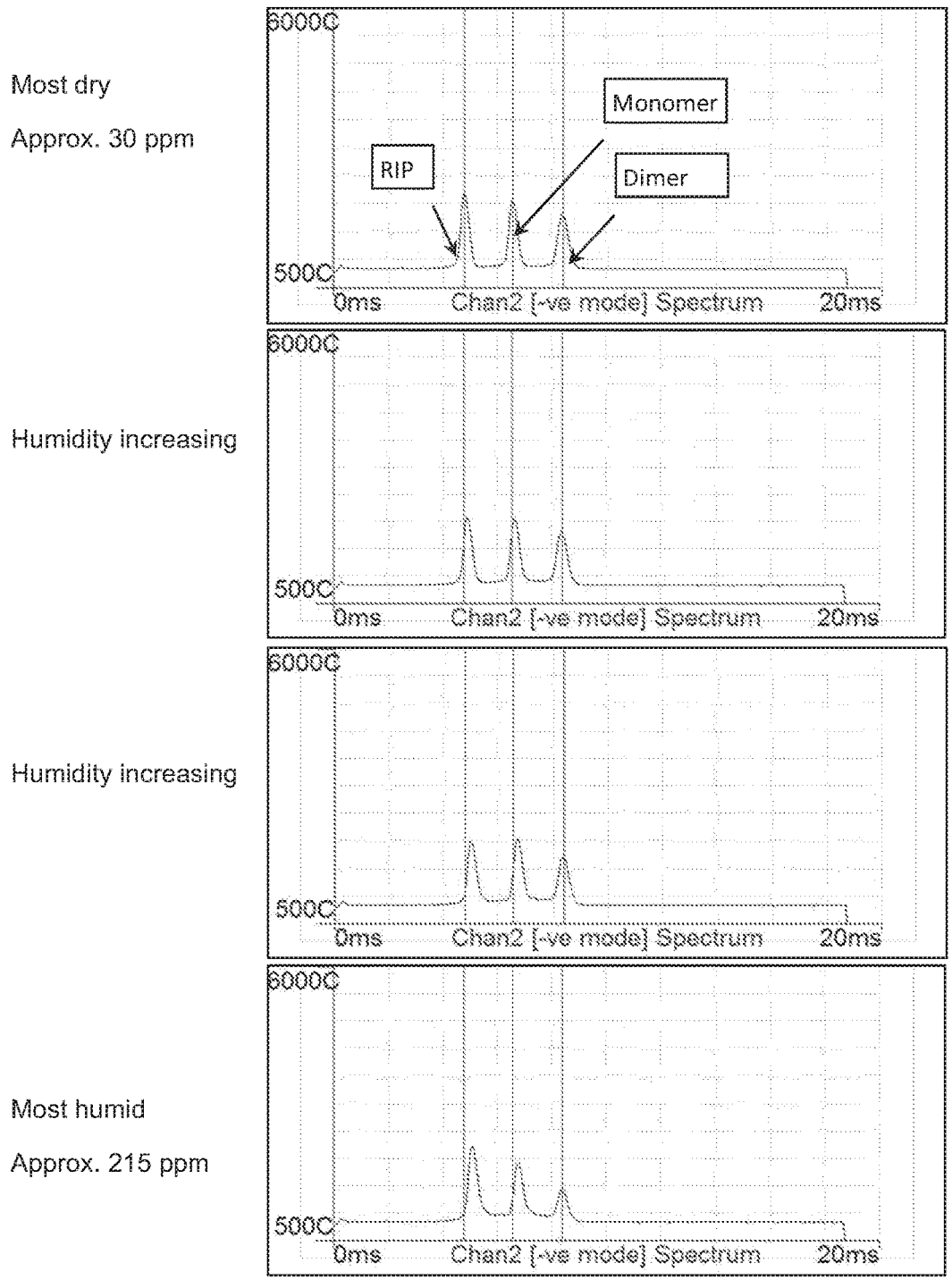

In the example illustrated in FIG. 1, the first part of the process 101 involves ionisation of a calibrant sample comprising or consisting essentially of isoflurane. Isoflurane, whose chemical structure is depicted below, is known principally for its use as an anesthetic, frequently used in veterinary anaesthesia, and typically exists in the form of a racemic mixture of (R) and (S) optical isomers.

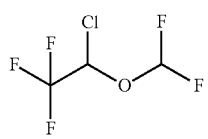

Thus, the calibrant sample is introduced into the detection apparatus where it is ionised by an ioniser of the detection apparatus. Upon ionisation, isoflurane may form negative monomer and dimer ions. Reference herein to a negative monomer ion of isoflurane and a negative dimer ion of isoflurane corresponds to $[CF_3CH(Cl)OCF_2H—X]^-$ and $[(CF_3CH(Cl)OCF_2H)_2—X]^-$ adducts respectively, wherein X is either $O_2$, Br or Cl. The nature of X in these adducts is dependent on the dominant chemistry within the detector which may, for instance, be modified by the presence, or absence, of a dopant during operation of the detector.

It is has been found by the inventors that the nature of the monomer and dimer ions is such that they are affected differently by certain experimental conditions commonly associated with detection apparatuses. It is the relationship between the experimental data relevant to the detection of the two different ions which can be discerned and used for the calibration of a detection apparatus for the detection of a particular target chemical.

In the process example illustrated in FIG. 1, there is detection 102 of the negative isoflurane monomer ion and negative isoflurane dimer ion by a detector of the detection apparatus suitable for detecting ions formed as a result of ionisation. In some embodiments, the detection apparatus comprises: a drift chamber between the ioniser and detector along which ions can travel from the ioniser toward the detector; a gate for controlling the passage of ions from the ioniser to the drift chamber; and a plurality of electrodes configured to provide a negative uniform electric field gradient within the drift chamber for transporting ions from the ioniser toward the detector. The detector may be linked to an analysis unit. In some embodiments, the analysis unit comprises a computer system. Said computer system may comprise computer program products, and may be recorded on non-transitory computer readable media, and these may be operable to program a processor to perform any one or more of the processes described herein.

The process illustrated in FIG. 1 comprises collection of data 103 relevant to the detection of the negative isoflurane monomer and dimer ions formed as a result of ionisation of the calibrant sample. In embodiments where the detection apparatus comprises a drift chamber between the ioniser and detector; a gate and a plurality of electrodes, the experimental data obtained as part of the process of the present disclosure may comprise drift times through the drift chamber for negative isoflurane monomer and dimer ions formed as a result of ionisation of the calibrant sample. In other words, the drift time corresponds to the time of flight of the monomer and dimer ions in the drift chamber following ionisation and up to detection. Where the detector is linked to an analysis unit, the analysis unit may be configured to collect experimental data relevant to the detection of isoflurane monomer and dimer ions formed as a result of ionisation of the calibrant sample.

The process illustrated in FIG. 1 comprises calibration of the detection apparatus 104 for a known target chemical based on an evaluation of the experimental data collected for the isoflurane monomer ion against the experimental data collected for the negative isoflurane dimer ion. In some embodiments, this part of the process may comprise evaluating the drift time of the negative isoflurane monomer against the drift time of the negative isoflurane dimer ion. In some embodiments, a level of clustering of neutral molecules in the detection apparatus about the isoflurane monomer ion is determined using the ratio of the isoflurane monomer ion drift time to isoflurane dimer ion drift time.

Calibration may thus comprise modifying the drift time detection parameter of the detector for the detection of a particular known target chemical. This may, for instance, be based on a comparison of a determined level of clustering of neutral molecules in the detection apparatus about the isoflurane monomer ion against predetermined drift times of the target chemical for varying levels of clustering. Once the detection apparatus has been calibrated, an analyte sample may be analysed using the detection apparatus with the modified detection parameter. Where an analysis unit is implemented as means for carrying out the process of the present disclosure, this analysis unit may be configured to calibrate the detection apparatus for the detection of a known target chemical based on an evaluation of the experimental data collected for the isoflurane monomer ion against the experimental data collected for the isoflurane dimer ion.

In some embodiments, the detection apparatus to be calibrated in accordance with the present disclosure is an ion mobility spectrometer, more particularly a negative mode ion mobility spectrometer. Ion mobility spectrometry (IMS) is an analytical technique that is capable of separating gas-phase ions according to their size to charge ratios as a result of interaction of the ions with a buffer gas in an electric field. IMS is capable of identifying chemicals based on the time taken for the ionised chemical to traverse a drift chamber separating an ioniser and a detector. The output of an IMS detector can be visually represented graphically as a spectrum of peak height versus the ion's time of flight ("drift time").

Ion mobility spectrometers have been utilised in numerous applications, most notably in the detection of chemical warfare agents, explosives and illicit drugs, due to their high sensitivity, portability, facile operation and fast response time, which have made them invaluable devices for military, police and security personnel. Ion mobility spectrometers have also been used in the detection of biological materials, including as part of medical diagnostic devices, as well as for the continuous monitoring of airborne molecular contamination.

FIG. 2 is an illustration of an ion mobility spectrometer 200 which includes an ionisation chamber 202 that is separated from a drift chamber 204 by a gate 206. The gate 206 can control passage of ions from the ionisation chamber 202 into the drift chamber 204. In FIG. 2, an ionisation source 210 is arranged for ionising material in the ionisation chamber 202. In the example illustrated in FIG. 2, the drift chamber 204 lies between the ionisation chamber 202 and a detector 218, so that ions can reach the detector 218 by traversing the drift chamber 204. The drift chamber 204 may comprise a series of electrodes 220 for applying an electric field in the drift chamber to move ions from the ionisation chamber 202 along the drift chamber 204 toward the detector 218. The ion mobility spectrometer 200 may be configured to provide a flow of buffer gas in a direction generally opposite an ion's path of travel to the detector 218. For example, the drift gas can flow from adjacent the detector 218 toward the gate 206.

The detector 218 may be used to characterise the ions detected based on the time for ions to pass from the gate 206 along the drift chamber 204 to the detector 218. Examples of a detector 218 are configured to provide a signal indicating that ions have arrived at the detector 218. For example, the detector may comprise a faraday plate, which generates an electrical current when ions are neutralised against it.

Electrodes 220 may be arranged to guide ions toward the detector 218, for example the electrodes 220 may comprise rings which may be arranged around the drift chamber 204 to focus ions onto the detector 218. Although the example of FIG. 2 includes a plurality of electrodes 220, in some examples only two electrodes may be used, or a single electrode may be used in combination with the detector 218 to apply an electric field to guide ions toward the detector 218. Other electrode configurations are also possible, examples include, but are not limited to electrodes of other geometric shapes and electrically resistive and/or conductive (e.g., a resistive electrical conductor) coatings, such as a continuous coating.

IMS may be operated, although not simultaneously, either in a negative mode or a positive mode, depending on whether a negative or positive electric field gradient is applied respectively. Historically, detection of analytes forming positive ions in an ion mobility spectrometer, and thus detected in the positive mode, has predominantly related to the detection of narcotics whilst the detection of explosives more often occurs in the negative mode.

Figure 4:
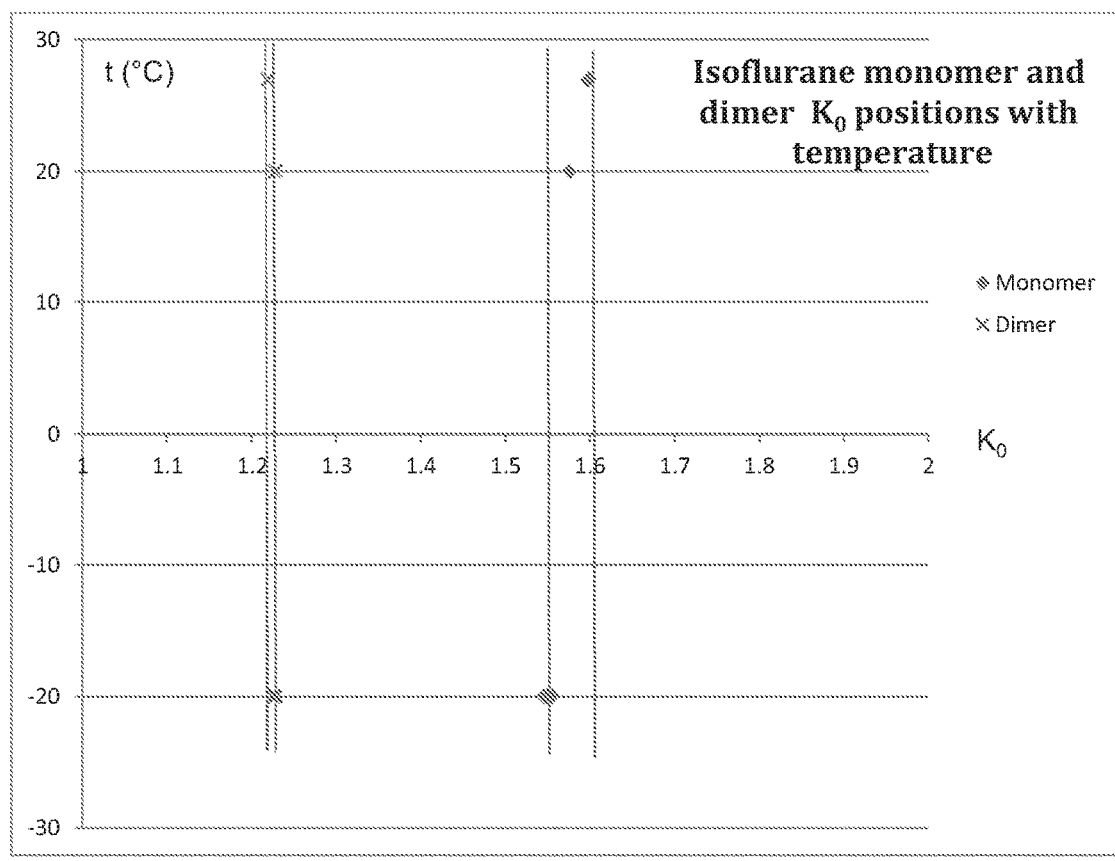
FIG. 4 is a plot showing the effect of temperature on reduced ion mobility ($K_0$) of the monomer and dimer ions of isoflurane.

The velocity of travel of ions in a buffer gas in the drift chamber 204 under the influence of an electric field is typically affected by field strength, nature of the buffer gas, temperature and pressure, in addition to the physical characteristics of the ion. A qualitative measure of a particular ion in the context of IMS is the ion mobility constant (K), which derives from the ion's velocity and the electric field strength, in accordance with equation (1) below:

$$K = \frac{v}{E} = \frac{L^2}{V \cdot t_d} \qquad (1)$$

where v is the velocity of the ion in cm s$^{-1}$, E the electric field in the drift region in V cm$^{-1}$, L the length of the drift region in cm, V the total voltage drop in volts across the drift region and $t_d$ the time taken ("drift time") for the ion to travel the distance L in seconds. Commonly, the ion mobility constant is modified and reported as a reduced mobility constant ($K_0$), which corresponds to a measured mobility constant corrected to standard pressure and temperature in accordance with equation (2) below:

$$K_0 = K \frac{P}{760} \frac{273}{T} = \frac{L^2}{V \cdot t_d} \frac{P}{760} \frac{273}{T} \qquad (2)$$

where P is the pressure in the drift region in Torr and T is the buffer gas temperature in Kelvin. One issue with equation (2) for determining reduced mobility is that it does not account for the effect of changes in the collision cross-section of ions as a result of changes in temperature (which effect is illustrated in FIG. 4, discussed below). As reported in Analyst, 2010, 135, 1433 to 1442, this has led to the use of chemical standards in IMS as a means for calibrating ion mobilities obtained experimentally. A number of chemical standards for use in IMS have been proposed in the past, including proton-bound dimers of 2,4-lutidine and dimethyl methylphosphonate, which exhibited little change in reduced mobility from ambient temperature up to 250° C.

Through the use of a chemical standard, reduced mobilities can be calculated from experimentally determined mobility values in accordance with equation (3) below. This relationship has in the past been used for correcting measurement uncertainties with respect to electric field strength, temperature and pressure in IMS.

$$\frac{K_{0\ (unknown)}}{K_{0\ (standard)}} = \frac{t_{d\ (standard)}}{t_{d\ (unknown)}} \qquad (3)$$

In recent years, it has been accepted that reduced mobility values are influenced not only by temperature and pressure, but also as a result of clustering of neutral molecules, such as water, air, carbon dioxide and volatile organic compounds, around ions traversing the drift chamber. In some instances, this may be the result of contamination of the buffer gas. Clustering around an ion affects its mobility through the drift chamber. This phenomenon has been shown, for instance, to affect the mobility of the proton-bound dimers of 2,4-lutidine and dimethyl methylphosphonate, which have previously been used as chemical standards.

As a consequence, there has been increased interest in chemical standards which are only weakly affected by clustering of neutral molecules, for instance as a result of high levels of moisture in the drift chamber associated with high humidity. This has also led to a new approach to the calibration of ion mobility spectrometers; one which relies on the use of a 'mobility standard' as well as an 'instrument standard', as proposed in Analyst, 2010, 135, 1433 to 1442. A mobility standard corresponds to a chemical standard which is sensitive to clustering, meanwhile a standard which is not susceptible to clustering, and thus whose mobility values remain for instance unaffected by contamination of the buffer gas, is deemed to be an instrument standard. Di-tert-butylpyridine (DTBP) has been identified as an example of an instrument standard for IMS, since its mobility is independent of buffer gas temperature and moisture level.

Calibration of an ion mobility spectrometer, such as that illustrated in FIG. 2, with a mobility and instrument standard, may first involve the determination of an instrument constant (Ci) using equation (4) below (a rearrangement of equation 2 above). It is proposed that the value of the instrument constant be determined following a change in the length of the drift region, pressure, temperature and/or electric field gradient.

$$K_{0,standard} \cdot t_{d,standard} = \frac{L^2}{V} \frac{P}{760} \frac{273}{T} = C_i \qquad (4)$$

Following determination of the instrument constant (Ci), a mobility standard may subsequently be used to determine whether there is clustering taking place in the spectrometer. If the product of the experimentally determined drift time of the mobility standard and its reduced mobility constant equals the determined instrument constant (Ci), then this is indicative of there being no clustering. In that case, equation (5) below may be used to determine the reduced mobility value of an unknown analyte.

$$K_{0,unknown} = \frac{C_i}{t_{d,unknown}} \qquad (5)$$

Alternatively, if there is clustering, for instance as a result of contamination in the spectrometer, then a correction factor, which would be unique to the particular analyte, at a specific temperature and level of clustering, may be determined to account for the effect of clustering on ion mobility. Ion mobility is principally affected by clustering as a result of its impeding effect on the travel of ions through the drift chamber. Such a correction factor may be used to calibrate the ion mobility spectrometer for the detection of a specific target chemical under the specific operating conditions of the spectrometer.

It has been found by the inventors that isoflurane alone may be effectively used as both an instrument standard and a mobility standard for determining the level of clustering in an ion mobility spectrometer and for calibrating for the detection of a particular target chemical. Isoflurane has been found to form two defined peaks in a negative mode ion mobility spectrometer, corresponding to monomer and dimer ions, $[CF_3CH(Cl)OCF_2H—X]^-$ and $[(CF_3CH(Cl)OCF_2H)_2—X]^-$ respectively, discussed hereinbefore. The dimer peak has been found to be only weakly susceptible to clustering with neutral molecules in the spectrometer, thereby corresponding to a form of instrument standard. Meanwhile, the mobility of the monomer peak has been found to be sensitive to clustering of neutral molecules in the spectrometer, thereby corresponding to a form of mobility standard. This is illustrated in the figures of the application.

FIG. 3 shows that when internal humidity, i.e. $H_2O$ content, is increased in the ion mobility spectrometer drift chamber (Top screen shot=30 ppm $H_2O$, Bottom screen shot=215 ppm $H_2O$), the extent of clustering around the isoflurane monomer ion increases, resulting in a corresponding increase in drift time. In contrast, the dimer ion is unaffected by clustering and therefore its drift time remains constant, despite the increase in humidity.

FIG. 4 shows a plot of isoflurane monomer and dimer ion reduced mobilities ($K_0$) measured in an undoped negative mode ion mobility spectrometer. It is clear that the isoflurane dimer ion is stable over the range of temperatures tested with no appreciable alteration of reduced ion mobility. In contrast, there is a notable increase in isoflurane monomer ion $K_0$ with increasing temperature. This is attributed to the loss of water of hydration, i.e. a reduction in the extent of water clustering about the monomer ion as temperature increases. FIG. 4 illustrates how a change in temperature can have a significant impact on monomer ion reduced mobility.

An instrument constant (Ci) can be determined for the particular conditions under which a spectrometer operates based on the experimentally determined drift time for the dimer ion of isoflurane. In turn, the instrument constant can be used to determine whether there is any clustering of neutral molecules about ions in the drift chamber by determining whether it is equal to the product of the experimentally determined drift time for the monomer ion of isoflurane and its reduced mobility constant. If the values are not equal, the extent of the difference can be used to quantify a level of clustering of neutral molecules about analyte ions within the spectrometer. Thus, in effect, the ratio of isoflurane monomer and isoflurane dimer mobilities can be used to determine the degree of clustering around the monomer.

This function of clustering can then be used to determine expected drift times for Product Ion Peak(s) (PIPs) of target chemicals which are susceptible to clustering, for which drift times have been predetermined for varying levels of clustering across a range of temperature. For example, the predetermined values may be derived from data obtained for drift times of PIPs at a number of particular combinations of temperature and humidity. It will be appreciated that such predetermined values may be readily obtained experimentally by the person of skill in the art. Alternatively, recourse may instead be made to modelling software packages which may use empirical data to model the effect of clustering on drift times of PIPs of target chemicals and to generate expected drift times for PIPs of target chemicals under the specific operating conditions of the detector. Such software is commercially available from different sources known to the person of skill in the art and accuracy thereof can readily be verified experimentally.

By determining the expected drift times for PIPs of a target chemical under the particular combination of experimental conditions, the detection parameters of the detector can be adjusted for detection of those PIPs at the expected drift times. For instance, the window position, corresponding to a range of drift time over which ion peaks may be visualised, can be adjusted so as to visualise the PIPs across a range of drift time which is appropriate having regard to the expected drift time of the target chemical's PIP(s). In this way, the spectrometer may be calibrated for the detection of a particular target chemical.

Thus, the calibration is a two stage process; firstly, the reduced mobility ($K_0$) of the dimer ion is used to calibrate $K_0$ space within the detector. Secondly, the $K_0$ of the monomer ion is used to determine the extent of clustering that is taking place within the cell, and detection windows are moved accordingly. The process of this disclosure may be performed in response to any change in pressure, temperature and/or electric field gradient whilst these parameters are continuously monitored during operation of the detection apparatus.

The present disclosure is suitable for the calibration of unheated and heated ion mobility spectrometers. However, the present disclosure is particularly suitable for the calibration of an unheated ion mobility spectrometer, which operates at ambient temperature. In view of the application of ion mobility spectrometers, often ambient temperature can be extremely wide ranging (e.g. well below 0° C. to over 40° C.). This range of temperature can have a significant effect on the peak positioning (drift time) of PIP(s) of target chemicals, as explained above. By fixing temperature, as in a heated ion mobility spectrometer, changes in peak positioning as a result of changing temperature are substantially reduced. However, in an unheated spectrometer, changes in ambient temperature can lead to significant shifts in peak positioning, as illustrated in respect of the isoflurane monomer ion in FIG. 4.

The process of the present disclosure enables detection parameters, for instance, window positioning, to be adjusted for detection of a target chemical across a wide range of ambient temperature, such as from −31° C. to 50° C., including from −10° C. to 40° C. Furthermore, isoflurane is also particularly advantageous in that it has a volatility which makes it suitable for use with an ion mobility spectrometer operating over a wide range of temperature.

The detection apparatus described herein may comprise a drying agent, such as a molecular sieve, for drying drift gas in the drift chamber. Moreover, as will be appreciated by the person of skill in the art, scrubbers may be employed to minimise contamination by volatile organic material. These components may reduce contamination in the drift chamber and/or the level of clustering of neutral molecules about ions in the drift chamber.

It will be appreciated that the ionisation source of the detection apparatus may be selected from any suitable source for the purposes of ionisation. For instance, radioactive sources may be used, such as a $^{63}Ni$ foil, electrospray ionisation, corona-spray and corona-discharge ionisation, matrix assisted laser desorption ionisation, or photoionisation sources. In some embodiments of the present disclosure, a doping agent (dopant) may be used to promote ionisation and, for instance, the formation of the negative isoflurane ion adducts described hereinbefore. Suitable dopants include hexachloroethane (HCE; CAS#67-72-1) and pentachloroethane (PCE; CAS#76-01-1).

The detector in the detection apparatus of the present disclosure may simply be a plate that works as a Faraday cup. However, it will be appreciated that other detectors may be used in accordance with the present disclosure as an alternative or in addition thereto, for example a mass spectrometer.

A means may also be provided with a detection apparatus which is configured for introducing the calibrant sample into the detection apparatus in response to a change in temperature, pressure and/or electric field of the detection apparatus. Detection apparatuses may include a vapour generator to supply a dopant chemical to the detector. Vapour generators can also be used to supply a test chemical for use in testing or calibrating a detector, a filter or other equipment. In some applications it is important that the vapour generator can be switched on and off rapidly, and that leakage can be prevented when the detector is switched off. For example, in an ion mobility spectrometer, rapid switching of the vapour generator on and off enables rapid switching between different doping conditions, such as different levels of dopant or different dopant substances. Such rapid switching could also enable different regions of the IMS detector to be doped differently by ensuring there was no leakage to undoped regions of the apparatus when the apparatus is switched off.

To improve the ability of a spectrometer to identify ions in a sample of interest, it is suggested to modify some of the ions using a radio frequency, RF, electric field (e.g. by fragmenting them) to provide additional information which can be used to infer an identity for the ions. This provides additional degrees of freedom in the measurement of the ions, and therefore may improve the ability to resolve differences between ions. Where measurements are performed in the presence of contaminants, or in difficult operating conditions, or where a sample comprises different chemical species' ions with similar geometries and masses etc. the ion mobility spectrometer's ability to detect and identify ions may be compromised, and ion modification is one way to address these issues.

In aspects of the present disclosure, a calibrant sample may be introduced into the detection apparatus by means of an on-demand vapour generator comprising: a vapour source comprising the calibrant sample coupled by a flow path to provide vapour through an impeder to an outlet for dispensing vapour to the detection apparatus. The impeder may comprise: a first vapour permeable passage arranged to impede diffusion of the vapour from the source to the outlet. The first vapour permeable passage may comprise a material adapted to take up the vapour, such as by absorption. Absorption comprises at least one of adsorbing the vapour onto a surface, chemical absorption, take up of the vapour by chemical or molecular action, and at least temporary capture of the vapour in a porous material. The vapour permeable passage is configured to enable vapour to be driven through a diffusion barrier from the source to the outlet by a pressure difference (e.g. pumped or forced flow as opposed to simply a difference in concentration).

The vapour generator may also comprise at least one additional vapour permeable passage to act as a sink, coupled to the outlet by the first vapour permeable passage. The sink can comprise a material adapted to take up the vapour to divert diffusion of vapour away from the outlet. In some embodiments, the first vapour permeable passage and the sink are arranged so that, in response to a pressure difference between the outlet and the vapour source, resistance to driving vapour flow through the first vapour permeable passage to the outlet is less than the resistance to driving vapour flow into the sink. In some embodiments, the flow path comprises a branch that couples the vapour source to the first vapour permeable passage, and an enclosed branch comprising the sink. In some embodiments, the sink comprises at least one second vapour permeable passage, the vapour source comprises a vapour chamber, and the impeder comprises an absorption assembly.

In one or more implementations, the vapour generator includes a vapour chamber configured to produce a vapour and a vapour absorption assembly configured to receive flows of vapour from the vapour chamber, for example via a diffusion barrier. The vapour absorption assembly includes a first vapour-permeable passage having a passage outlet. The vapour absorption assembly may further include one or more second vapour-permeable passages that are closed. When the vapour absorption assembly receives a flow (e.g. a pressure driven flow) of vapour from the vapour chamber, the flow of vapour passes through the first vapour-permeable passage to the passage outlet at least substantially without absorption of vapour from the flow of vapour. However, when a flow of vapour is not received from the vapour chamber, vapour entering the vapour absorption assembly from the vapour chamber passes into the first vapour-permeable passage and then at least one second vapour-permeable passage and is at least substantially absorbed.

FIGS. 5 through 8 illustrate on-demand vapour generators 500 in accordance with example implementations of the present disclosure. As shown, the vapour generator 500 includes an inlet 502 and a vapour outlet 503 connected to an inlet of a detector apparatus 504. The vapour generator 500 is configured to furnish a readily controllable supply of vapour to the detector apparatus 504. In implementations, the vapour generator 500 may supply a flow of vapour to a variety of detector apparatus. For example, in one implementation, the detector apparatus 504 may comprise an IMS detector. In implementations, the vapour generator 500 and detector apparatus 504 may be part of a detection system (e.g., an IMS detection system) 50. In such detection systems 50, the vapour generator 500 and the detector assembly can be housed within a common housing.

The vapour generator 500 includes a gas (e.g., air) flow generator 506 such as a fan, a blower, a compressed gas source, and so forth. The flow generator 506 is configured to be switched on or off to provide a flow of gas (air) to its outlet 507 as desired. The flow generator 506 may include various filters or other devices to remove contaminants and water vapour from the gas (e.g., from atmospheric air) before the gas is supplied to the outlet 507.

The outlet 507 of the flow generator 506 is in fluid communication with (e.g., is coupled to) an inlet 508 at one end of a vapour chamber 509. The vapour chamber 509 may have a variety of configurations, and may comprise any kind of vapour source, or a permeation source, for example a diffusion source. For example, in the implementation shown, the vapour chamber 509 includes a housing 510 that contains a wicking, absorbent material 511 saturated with a compound, for example isoflurane, in its liquid phase so that the space of the interior 512 within the housing 510 above the absorbent material 511 is at least substantially filled with a vapour of the liquid at the liquid's saturated vapour pressure at ambient temperature. The vapour chamber 509 includes an outlet 513 at the end opposite the inlet 508 through which a flow of vapour, comprised of the vapour and gas, can flow out of the vapour chamber 509.

The vapour chamber outlet 513 is in fluid communication with (e.g., is coupled to) an inlet 514 of a vapour absorption assembly 515, for example via a diffusion barrier. The vapour absorption assembly 515 includes a vapour absorbent 516 configured to absorb the vapour produced by the vapour chamber 509. A vapour-permeable passage (main flow path) 517 having an outlet (vapour outlet 503) extends through the vapour absorbent 516 and is coupled to the detector apparatus 504. In the illustrated implementations, the vapour absorption assembly 515 includes a single vapour-permeable passage 517. However, it is contemplated that additional vapour-permeable passages 517 may be provided in parallel to the passage 517 shown. Moreover, a second vapour absorption assembly can be provided between the inlet 508 of the vapour chamber 509 and the flow generator 506 to prevent vapour from the chamber 509 passing to the flow generator 506 in significant quantities when the flow of gas is off (e.g., when the flow generator 506 is turned off). A pneumatic valve can be connected between this second vapour absorption assembly and the vapour chamber. This valve may be maintained closed until gas (air) flow is required.

The on demand vapour generator 500 may further include one or more diffusion barriers 505. In implementations, the diffusion barriers may comprise flow paths with a small cross sectional area that limit the rate of diffusion (and therefore loss) of vapour from the vapour generator 500 when the generator 500 is in the off-state (e.g., when no flow of vapour is furnished by the vapour generator 500).

When the vapour generator 500 is off (e.g., is in the "off" state, that is, when no flow of vapour is provided), the flow generator 506 remains off so that there is no flow of gas (air) through the vapour chamber 509 and the vapour-permeable passage 517. The vapour-permeable passage 517 is open to the interior 512 of the vapour chamber 509 so that some vapour may drift into the passage 517. As this drift occurs, the vapour diffuses into the vapour-absorbent material and is absorbed therein. The bore, length, porosity and nature of the vapour absorbent 516 are chosen such that, under zero flow conditions (e.g., no or virtually no flow conditions), the amount of vapour that escapes from the outlet 503 end of the passage 517 is insignificant in the context of the application in which the vapour generator 500 is used. For example, where the vapour generator 500 is used as a calibrant source in an IMS detector, the vapour calibrant flow in the off state is arranged to be not sufficient to produce any noticeable calibrant ion peak by the IMS detector.

The vapour generator 500 is turned on to produce a flow of vapour at its outlet 503 by turning on the flow generator 506 to produce a flow of gas (air) into the inlet 508 of the vapour chamber 509. This flow of gas (air) collects the vapour produced in the vapour chamber 509 and pushes it through the outlet 513 and into the passage 517 of the vapour absorption assembly 515. The flow velocity in the passage 517 is chosen such that the residence time of the collected vapour in the passage is sufficiently low so that little vapour is absorbed into the vapour absorbent 516. Thus, a greater proportion of the vapour passes through the vapour-permeable passage 517 to the outlet 503 end of the passage 517 to be delivered to the detector apparatus 504 than when the flow generator is off. The flow of vapour can be continuous or pulsed.

The vapour generator 500 is configured to be capable of turning off vapour flow very rapidly when not required, such that the vapour does not leak out at a significant rate. In an IMS detection system, this effectively prevents dopant vapour from entering the IMS detector when the system is turned off and is not powered. This can also enable selected regions of IMS detector to be doped with a reduced risk that dopant will leak to undoped regions when the apparatus is turned off. In conventional systems, gas flow through the IMS detector can keep undoped regions free of dopant when the apparatus is powered but, when not powered, the gas flow ceases and any slight leakage of dopant will contaminate all regions of the apparatus. This has previously made it very difficult to dope different regions of IMS detector differently except where the apparatus is continuously powered.

In FIGS. 5 through 8, the flow generator 506 is illustrated as being in fluid communication with (e.g., connected to) the inlet 502 of the vapour chamber 509 to push air into the chamber 509. However, in other implementations, the flow generator 506 may be connected downstream of the vapour chamber 509 and be arranged to pull air into the chamber 509. For example, the flow generator 506 may be connected between the outlet 513 of the vapour chamber 509 and the inlet 514 of the vapour absorption assembly 515 (the inlet 514 end of the vapour-permeable passage 517), or it could be connected downstream of the vapour absorption assembly 515 (at the outlet 503 end of the passage 517).

Figure 7:
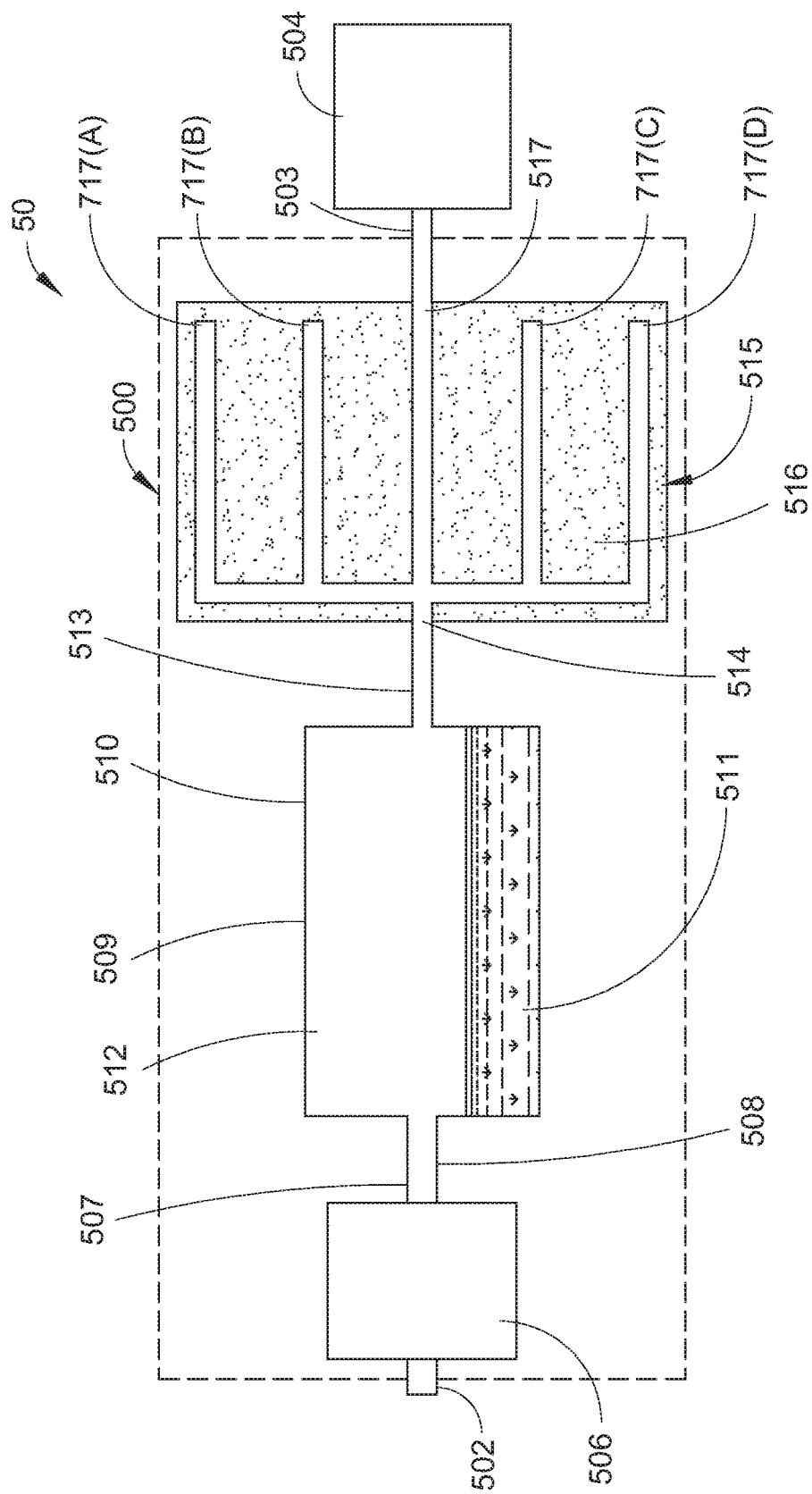
FIG. 7 is a schematic block diagram that illustrates an example of an on-demand vapour generator (OVG) which may be used for introducing the isoflurane calibrant sample into a detector apparatus, wherein the on-demand vapour generator employs a vapour-permeable passage having a passage outlet and one or more vapour-permeable passages that are closed.
Figure 8:
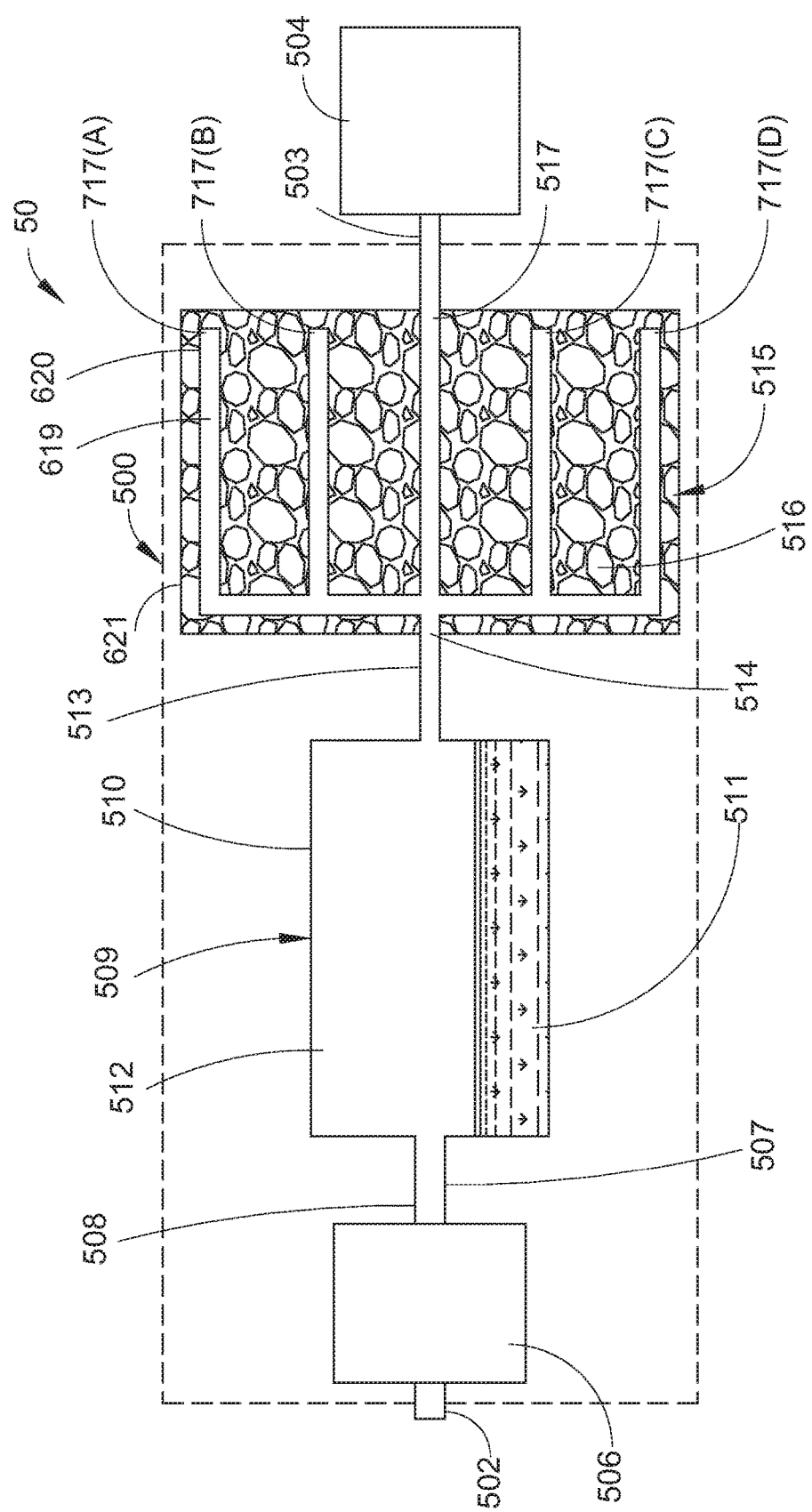
FIG. 8 is a schematic block diagram that illustrates another example of an on-demand vapour generator (OVG) which may be used for introducing the isoflurane calibrant sample into a detector apparatus, wherein the on-demand vapour generator employs a vapour-permeable passage having a passage outlet and one or more vapour-permeable passages that are closed.

In the implementations shown in FIGS. 7 and 8, the vapour absorption assembly 515 is illustrated as further including one or more additional vapour-permeable passages (region) that are closed (e.g., blocked) so as to form "dead end" vapour-permeable passages (four (4) dead end vapour-permeable passages 717A-D, collectively 717, are illustrated). As shown, the dead end vapour-permeable passages 717 may thus extend only partially through the vapour absorbent 516, and do not include outlets.

When the vapour absorption assembly 515 receives a flow of vapour from the vapour chamber 509 (e.g., the flow generator 506 is turned on), the flow of vapour passes through the primary vapour-permeable passage 517, which functions as a main flow path, to the passage outlet 503 at least substantially without absorption of vapour from the flow of vapour by the vapour absorbent 516. However, when a flow of vapour is not received from the vapour chamber (e.g., the flow generator 506 is turned off so that there is negligible or no flow of vapour), vapour entering the vapour absorption assembly 515 from the vapour chamber 509 passes into the vapour-permeable passage 517 and/or the dead end vapour-permeable passages 717 and is at least substantially absorbed by the vapour absorbent 516.

When the vapour generator 500 is in the off-state (e.g., when no flow of vapour is supplied), vapour diffusing out of the vapour chamber 509 enters the vapour absorption assembly 515 as before, but now passes down both the vapour-permeable passage 517 (main flow path) and the dead end vapour-permeable passages 517. As a result, the area of absorption provided for the vapour (and therefore the extent of absorption) is greatly increased. However, when the vapour generator 500 is in the on-state (e.g., when a flow of vapour is supplied), the dead end vapour-permeable passages 717 act as dead volumes with essentially no gas exchange and do not contribute to the absorption of vapour from the flow of vapour. Therefore, there is no significant change in the concentration of vapour exiting the vapour generator 500 with the dead end vapour-permeable passages 717 from implementations that include only the vapour-permeable passage 517 without the dead end vapour-permeable passages 717.

In implementations, the addition of dead-end vapour-permeable passages 717 allows the width of the temperature range over which the on-demand vapour generator 500 can be operated to be increased. As temperature increases, the activity of permeation and diffusion sources rise, the rate of diffusion rises, and the ability of absorbent materials (e.g. activated charcoal) to capture chemicals often decreases. Consequently, a greater concentration of vapour, at a higher rate, is delivered to the vapour absorption assembly 515 of the vapour generator 500. This increase will be compounded by the reduction in absorption capacity/rate, leading to the vapour absorption assembly 515 being less capable of dealing with the vapour. Leakage in the off-state may therefore increase. Therefore, when the vapour-permeable passage 517 of the vapour absorption assemblies 515 shown in FIGS. 5 and 6 (without dead end vapour-permeable passages 717) are designed to be of suitable length to allow an adequate concentration of vapour to exit the vapour generator 500 in the on-state at extremely low temperatures, the passages 517 may not be adequately long to absorb all vapour in the off-state at extremely high temperatures. The addition of dead end vapour-permeable passages 717 to the vapour absorption assembly 515, as shown in FIGS. 7 and 8, increases the off-state absorption while not decreasing the on-state vapour concentration exiting the vapour generator 500. Accordingly, the addition of dead end vapour-permeable passages 717 to the vapour absorption assembly 515 makes it possible to reduce the leakage of vapour over a greater range of temperatures without limiting the ability of the vapour generator 500 to supply adequate vapour at extremely low temperatures. Moreover, the additions of dead end vapour-permeable passages 717 makes it possible to further increase the concentration of the vapour leaving the vapour generator 500 without compromising the ability of the vapour generator 500 to restrict the leakage of vapour in the off-state.

Figure 5:
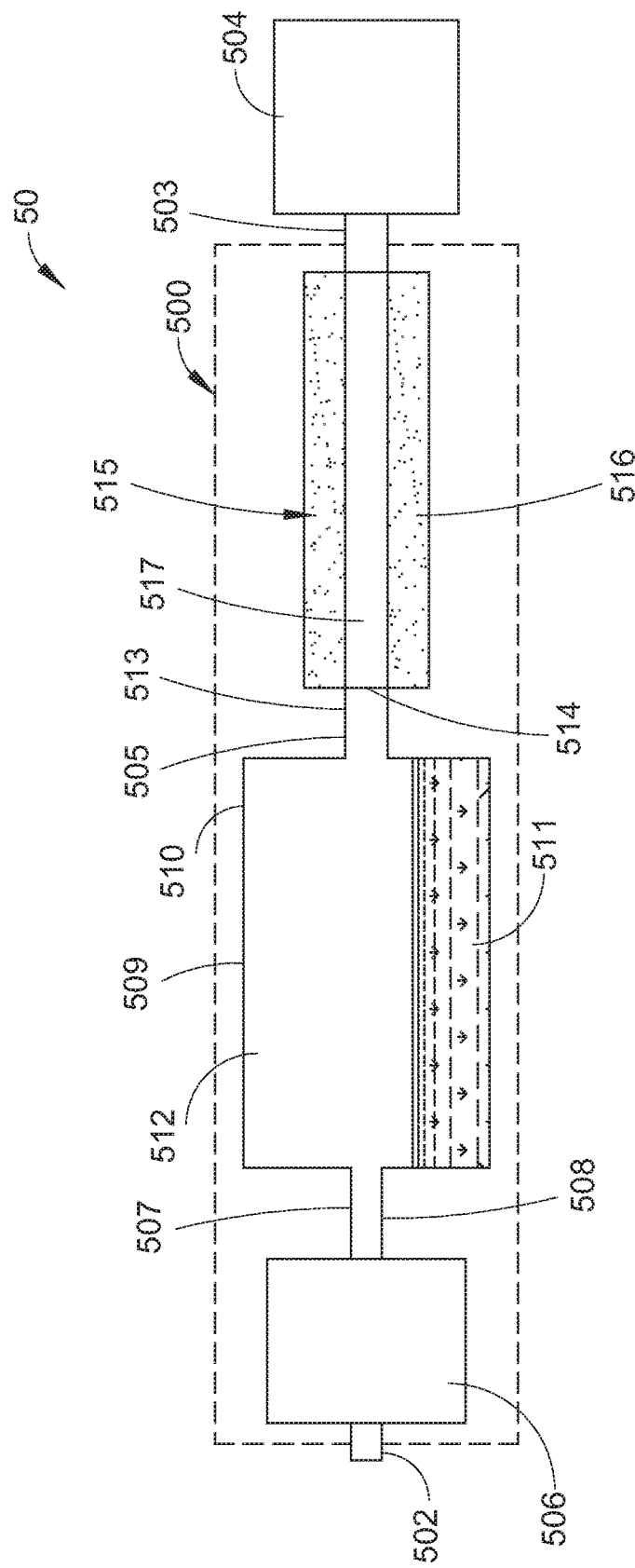
FIG. 5 is a schematic block diagram that illustrates an example of an on-demand vapour generator (OVG) which may be used for introducing the isoflurane calibrant sample into a detector apparatus, wherein the on-demand vapour generator employs a single vapour-permeable passage.
Figure 6:
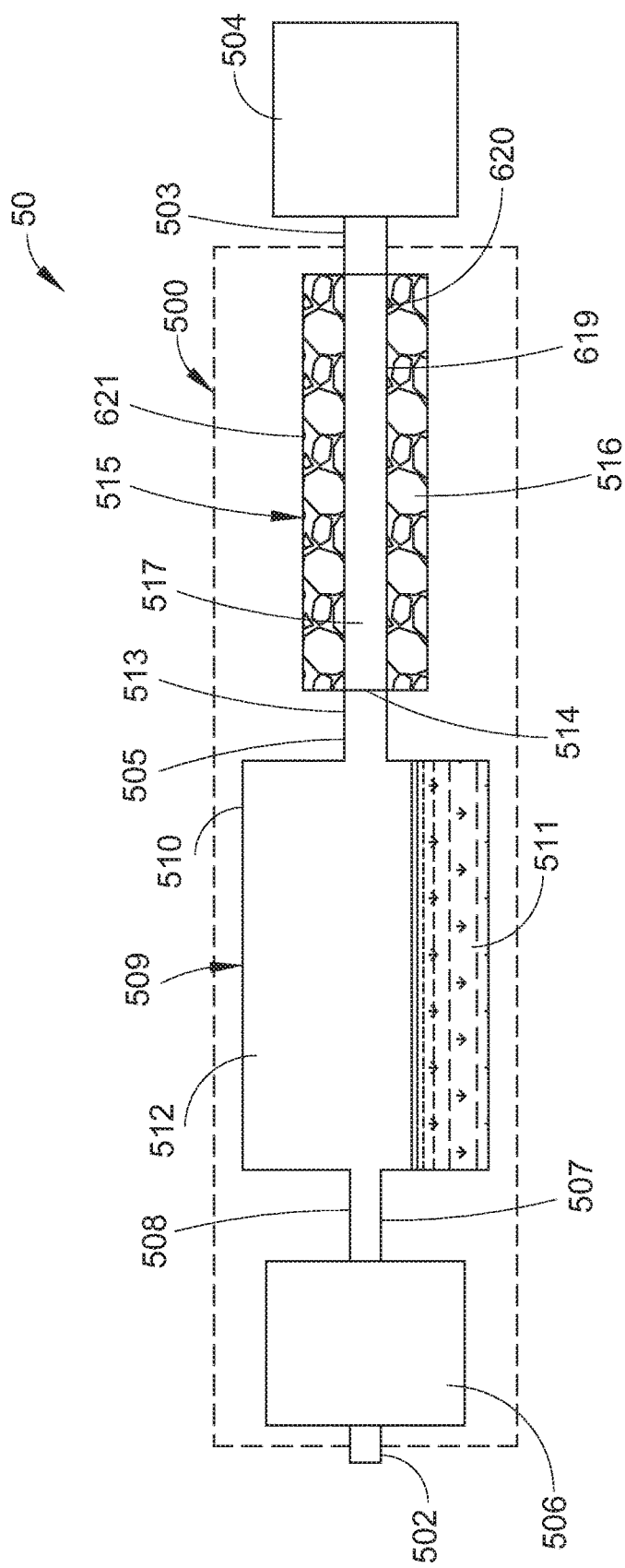
FIG. 6 is a schematic block diagram that illustrates another example of an on-demand vapour generator (OVG) which may be used for introducing the isoflurane calibrant sample into a detector apparatus, wherein the on-demand vapour generator employs a single vapour-permeable passage.

In implementations, addition of dead end vapour-permeable passages 717 to the vapour absorption assembly 515, as shown in FIGS. 5 and 6, may facilitate shortening of the main flow path (e.g., shortening of the vapour-permeable passage 517) to allow higher vapour concentrations to be produced by the vapour generator 500 in the on-state without limiting the ability of the generator 500 to limit leakage in the off-state. Moreover, in situations where the detection system 50 is to be operated over a range of temperatures, the addition of dead end vapour-permeable passages 717 to the vapour absorption assembly 515 enhances the ability of the vapour generator 500 to furnish an adequate concentration of vapour exiting the vapour generator 500 in the on-state at low temperature by having a short main flow path (when the activity of the source is lower than at high temperature), while simultaneously restricting the leakage of the vapour generator 500 in the off-state to acceptable levels at higher temperatures (when the activity of the source and the rate of diffusion are higher than at low temperatures).

The dimensions, layout and configuration of the vapour absorption assemblies 515 of the on-demand vapour generators 500 shown in FIGS. 5 through 8, including the vapour-permeable passage 517 (main flow path) and/or the dead end vapour-permeable passages 717 may vary depending on a variety of factors including, but not limited to: the activity of the vapour source (vapour chamber 509), the required concentrations to be provided, the flows used in the on-state of the vapour generator 500, the acceptable level of release when in the off-state and the conditions (e.g. temperature) under which the vapour generator 500 is to be operated. Accordingly, any dimensions, layouts, or configurations presented herein are for illustrative purposes, and are not necessarily meant to be restrictive of the disclosure.

In implementations shown in FIGS. 5 and 7, the vapour-permeable passage 517 and/or the dead end vapour-permeable passages 717 of the vapour absorption assembly 515 comprise machined bores formed in a block 516 of an absorbent material such as carbon (e.g., activated charcoal) or a sintered material, such as a molecular sieve material, which could be of zeolite. In other implementations, the vapour-permeable passage 517 and dead end vapour-permeable passages 717 may be formed by moulding the block 516 about a core structure that is subsequently removed. The absorbent material is configured to be absorbent of the vapour (e.g., of acetone vapour, and so forth). For example, the material may itself be formed of an absorbent material, such as carbon (e.g., activated charcoal), or the material itself may be a non-absorbent material rendered absorbent via impregnation with a suitable substance. In this manner, the vapour (e.g., acetone vapour, and so forth) may be absorbed by the vapour absorbent 516 generally along the length of the vapour-permeable passage 517 and within the dead-end vapour-permeable passages 717.

In the implementation shown in FIGS. 6 and 8, the vapour-permeable passage 517 and/or the dead end vapour-permeable passages 717 comprise lengths of tube 619 having a vapour-permeable outer wall or membrane 620 that are at least substantially enclosed within an outer housing 621 formed of a vapour-impermeable material. For example, as shown, the tube 619 forming the vapour-permeable passage 517 may extend axially along the center of the housing 621, while tubes 619 forming the dead end vapour-permeable passages 717 are arrayed around the central tube. As shown, the tube 619 that forms the vapour-permeable passage 517 includes a first end coupled to the inlet 514 and a second end coupled to the vapour outlet 503. Similarly, the tubes that form the dead end vapour-permeable passages 717 include first ends that are coupled to the inlet 514. However, the second ends of these tubes are blocked and do not extend from the housing 621. The bore, length, wall thickness and material of the tubes 619 may be chosen such that, under zero flow conditions, the amount of vapour that escapes from the outlet 503 end of the tube 619 is insignificant in the context of the application in which the vapour generator 500 is employed.

In one example, the tube 619 forming the vapour-permeable passage 517 shown in FIG. 6 is approximately one hundred millimeters (100 mm) long with an external diameter of approximately one millimeter (1 mm), and an internal diameter of approximately one half millimeter (0.5 mm). However, tubes 619 having other sizes are contemplated. The volume between the outside surface of the tubes 619 and the inside surface of the housing 621 is at least substantially filled with a material 516 that readily absorbs the vapour produced by the vapour chamber 509. In implementations, the material 516 may comprise activated charcoal granules that are effective to absorb vapour, such as acetone vapour, or the like. Thus, the tubes 619 may be surrounded on all sides by the absorbent charcoal granules. In implementations, the tubes 619 may be formed of an elastomeric plastic, such as silicone rubber, and so forth.

In implementations, the on-demand vapour generator 500 may further include a pneumatic valve connected to block flow of vapour from the vapour chamber 509 to the absorbent passage until vapour flow is employed. The pneumatic valve would have the advantage of preventing continual adsorption of the vapour into the vapour absorbent 516, thus lengthening the life of both the vapour chamber 509 and the absorbent material of the vapour absorbent 516. The vapour-permeable passage 517 and/or the dead end vapour-permeable passages 717 may thus trap vapour that permeates through the valve seals, providing a lower rate of diffusion. Consequently, the size of the vapour absorbent assembly 515 (e.g., the length, surface area, etc. of the vapour-permeable passage 517 and/or the dead end vapour-permeable passages 717) may be reduced.

In FIGS. 5 through 8, the vapour absorbent 516 is illustrated as extending around the vapour-permeable passage 517 and/or the dead end vapour-permeable passages 717. However, in implementations, the entire vapour generator 500 may be at least substantially enclosed in a vapour absorbent so that vapour does not substantially escape from the vapour generator 500 in the off state.

The on-demand vapour generator 500 described herein provides for efficient trapping of vapour. The vapour generator 500 may be used to provide a periodic internal isoflurane calibrant in a detection system 50, such as an IMS detection system.

In a further aspect, the present disclosure also relates to a use of a calibrant sample comprising or consisting essentially of isoflurane for calibrating a detection apparatus as described hereinbefore for the detection of a target chemical.

Embodiments of the present disclosure described hereinbefore may be combined with any other compatible embodiments to form further embodiments of the disclosure.

The invention claimed is:

1. A process for calibrating a detection apparatus comprising:
   introducing a calibrant sample comprising isoflurane into a detection apparatus;
   collecting experimental data relevant to the detection of a negative isoflurane monomer ion and a negative isoflurane dimer ion formed as a result of ionisation of the calibrant sample; and
   calibrating the detection apparatus for the detection of a known target chemical based on an evaluation of the experimental data collected for the negative isoflurane monomer ion against the experimental data collected for the negative isoflurane dimer ion.

2. A process according to claim 1, wherein calibration of the detection apparatus comprises modifying one or more detection parameters of the detection apparatus.

3. A process according to claim 1, further comprising analysing an analyte sample using the detection apparatus after calibrating the detection apparatus for the detection of a known target chemical.

4. A process according to claim 1, wherein the detection apparatus comprises:
   an ioniser for ionising a sample;
   a detector for detecting ions formed as a result of ionisation;
   a drift chamber between the ioniser and detector along which ions can travel from the ioniser toward the detector;
   a gate for controlling the passage of ions from the ioniser to the drift chamber;
   a singularity or plurality of electrodes configured to provide a negative uniform electric field gradient within the drift chamber for transporting ions from the ioniser toward the detector;
   and wherein the experimental data comprises drift times through the drift chamber for the negative isoflurane monomer ion and the negative isoflurane dimer ion formed as a result of ionisation of the calibrant sample; and wherein calibrating the detection apparatus for the detection of a known target chemical comprises evaluating the drift time of the negative isoflurane monomer ion against the drift time of the negative isoflurane dimer ion.

5. A process according to claim 4, further comprising modifying a drift time detection parameter of the detector.

6. A process according to claim 4, wherein calibrating the detection apparatus for the detection of a known target chemical further comprises determining a level of clustering of neutral molecules about the negative isoflurane monomer ion.

7. A process according to claim 6, wherein the level of clustering is determined using the ratio of the negative isoflurane monomer ion drift time to the negative isoflurane dimer ion drift time.

8. A process according to claim 6, wherein the determined level of clustering is used to calibrate the detection apparatus for the detection of a target chemical by comparing the determined level of clustering against predetermined drift times of the target chemical for varying levels of clustering.

9. A process according to claim 4, further comprising introducing a dopant into the detection apparatus.

10. A process according to claim 4, wherein the detection apparatus further comprises a drying agent for drying drift gas in the drift chamber.

11. A process according to claim 1, wherein the calibrant sample is introduced into the detection apparatus in the form of a vapour.

12. A process according to claim 11, wherein the calibrant sample is introduced into the detection apparatus by means of a vapour generator comprising:
   a vapour source comprising the calibrant sample coupled by a flow path to provide vapour through an impeder to an outlet for dispensing vapour to the detection apparatus, wherein the impeder comprises:
   a first vapour permeable passage arranged to impede diffusion of the vapour from the source to the outlet and to enable vapour to be driven from the source to the outlet; and
   a sink separated from the outlet by the first vapour permeable passage wherein the sink comprises a material adapted to take up the vapour and is arranged to divert diffusion of vapour away from the outlet.

13. A process according to claim 12, wherein the first vapour permeable passage and the sink are arranged so that, in response to a pressure difference between the outlet and the vapour source, resistance to driving vapour flow through the first vapour permeable passage to the outlet is less than the resistance to driving vapour flow into the sink.

14. A process according to claim 12, wherein the flow path comprises a branch that couples the vapour source to the first vapour permeable passage, and an enclosed branch comprising the sink.

15. A process according to claim 12, wherein the first vapour permeable passage comprises a material adapted to take up the vapour.

16. A process according to claim 12, wherein the sink comprises at least one second vapour permeable passage, the vapour source comprises a vapour chamber, and the impeder comprises an absorption assembly.

17. A process according to claim 1, wherein calibration is performed in response to a change in at least one of temperature of the detection apparatus, pressure of the detection apparatus, or electric field gradient of the detection apparatus.

18. A system for calibrating a detection apparatus comprising:
a detection apparatus comprising:
an ioniser for ionising a sample;
a detector for detecting ions formed as a result of ionisation;
a calibrant sample comprising isoflurane; and
an analysis unit configured to:
collect experimental data relevant to the detection of an isoflurane monomer ion and an isoflurane dimer ion formed as a result of ionisation of the calibrant sample; and
calibrate the detection apparatus for the detection of a known target chemical based on an evaluation of the experimental data collected for the isoflurane monomer ion against the experimental data collected for the isoflurane dimer ion.

19. A system according to claim 18, further comprising a vapour generator configured for use with the detection apparatus, the vapour generator comprising:
a vapour source comprising the calibrant sample coupled by a flow path to provide vapour through an impeder to an outlet for dispensing vapour to the detection apparatus, wherein the impeder comprises:
a first vapour permeable passage arranged to impede diffusion of the vapour from the source to the outlet and to enable vapour to be driven from the source to the outlet; and
a sink separated from the outlet by the first vapour permeable passage wherein the sink comprises a material adapted to take up the vapour and is arranged to divert diffusion of vapour away from the outlet.

20. A device comprising:
a detection apparatus comprising:
an ioniser for ionising a sample;
a detector for detecting ions formed as a result of ionisation;
a calibrant sample comprising or consisting essentially of isoflurane; and
a vapour generator configured for introducing the calibrant sample into the detection apparatus in response to a change in at least one of temperature of the detection apparatus, pressure of the detection apparatus, or electric field of the detection apparatus.

* * * * *